United States Patent [19]

Sakai et al.

[11] Patent Number: 5,560,907
[45] Date of Patent: * Oct. 1, 1996

[54] WHITENING EMBELLISHER

[75] Inventors: Itaru Sakai; Kana Satoh; Tomohide Tanaka; Yutaka Morita; Takashi Hibi; Yoshio Tanabe; Shigemitsu Osawa, all of Saitama Prefecture; Yasushi Tomita, Miyagi Prefecture, all of Japan

[73] Assignee: Eisai Co., Ltd., Tokyo, Japan

[*] Notice: The term of this patent shall not extend beyond the expiration date of Pat. No. 5,427,775.

[21] Appl. No.: 403,174

[22] Filed: Mar. 13, 1995

Related U.S. Application Data

[62] Division of Ser. No. 32,259, Mar. 17, 1993, Pat. No. 5,427,775.

[30] Foreign Application Priority Data

Mar. 17, 1992 [JP] Japan ......................... 4-90090
Mar. 17, 1992 [JP] Japan ......................... 4-90091

[51] Int. Cl.$^6$ ........................................ A61K 7/48
[52] U.S. Cl. .......................... 424/62; 424/401; 424/464; 424/484; 424/489; 514/25; 514/460; 514/474; 514/675; 514/844; 514/846; 514/960
[58] Field of Search ....................... 424/62, 401, 464, 424/484, 489; 514/25, 460, 474, 675, 844, 846, 960

[56] References Cited

U.S. PATENT DOCUMENTS 4,814,353  3/1989  Itor et al. ........................ 514/645
5,427,775  6/1995  Sakai et al. ...................... 424/62

OTHER PUBLICATIONS

CA 116: 51521s (1992), "Effect Of Teprenone On Liver Injury Caused By Ischemia–Reperfusion".

*Primary Examiner*—Jyothsna Venkat
*Attorney, Agent, or Firm*—Wenderoth, Lind & Ponack

[57] ABSTRACT

A whitening embellisher includes, as an active ingredient, teprenone (chemical name: geranylgeranyl-acetone). A whitening and beautifying composition includes teprenone and one or more substances selected from kojic acid, L-ascorbic acid and the like.

The whitening embellisher, and whitening and beautifying composition prevent the skin from pigmenting and darkening due to sunburn and/or aging, and quicken fading, and hence make spots and freckles inconspicuous when the preparations are used for external application as a cream or milky lotion.

4 Claims, No Drawings

WHITENING EMBELLISHER

This is a divisional application of Ser. No. 08/032,259, filed Mar. 17, 1993, now U.S. Pat. No. 5,427,775.

BACKGROUND OF THE INVENTION

1) Field of the Invention

The present invention relates to a whitening embellisher which inhibits the production of melanin in the epithelia and the like, and more specifically to whitening embellishers suitable for external application and use in a bath.

2) Description of the Related Art

The whiteness and transparency of the skin have traditionally been basic requirements for polished beauty in Japan. In recent years, the development of some excellent materials has brought about common use of cosmetic preparations which directly act on the biosynthetic mechanism of melanin. For example, as compounds having an action to inhibit the activity of an oxidase, tyrosinase which promotes a melanin synthesis from tyrosin through dopachrom, there may be mentioned kojic acid, L-ascorbic acid and derivative thereof, various sulfur compounds, and the like. In addition, as a compound having an action to inhibit the synthesis of tyrosinase, there may be mentioned arbutin.

Common defects of these compounds are that since their actions themselves are mild, a continuous application for about 1 month is required to actually feel their effects, and from the viewpoint of their physical properties, they are highly soluble in water, tend to undergo oxidative decomposition and discoloration, and encounter difficulties upon providing stable preparations.

SUMMARY OF THE INVENTION

Therefore, it is an object of the present invention to provide preparations suitable for external application and use in a bath, which prevent the formation of melanin in the skin or the like and whiten the skin.

Another object is to more enhance and accelerate the development of the whitening and beautifying effect exhibited by kojic acid, L-ascorbic acid or the like.

The present inventors have noticed that teprenone has actions of, for example, protecting and repairing the mucous membrane, multiplying and activating cells, and accelerating the synthesis of phospholipids and combines extremely high stability with preferred natures from the viewpoint of physical properties, and hence have carried out an extensive investigation of teprenone in an experimental system making use of cultured cells. As a result, it has been found that teprenone which has been widely used as a remedy for gastric ulcer or gastritis to date surprisingly has an action to strongly inhibit the biosynthesis of tyrosinase.

The present inventors have conducted a further extensive investigation of teprenone. As a result, it has been found that teprenone develops a still stronger whitening and beautifying action by a synergism with the conventionally-known substance having a whitening and beautifying action, such as kojic acid or L-ascorbic acid.

The present invention has been completed on the basis of these findings.

In an aspect of the present invention, there is thus provided a whitening embellisher comprising, as an active ingredient, teprenone.

The whitening embellisher may preferably be a preparation suitable for external application or use in a bath, which has an action to whiten and beautify the skin.

In another aspect of the present invention, there is also provided a whitening and beautifying composition comprising (1) teprenone and (2) one or more substances selected from kojic acid, L-ascorbic acid and arbutin, and derivatives thereof and having a whitening and beautifying action.

The whitening and beautifying composition of the present invention means a whitening and beautifying preparation suitable for external application, use in a bath, or the like.

Other objects and advantages of the present invention will be readily appreciated from the preferred embodiments of the present invention, which will be described subsequently in detail.

DETAILED DESCRIPTION OF THE INVENTION AND PREFERRED EMBODIMENTS

Teprenone useful in the practice of the present invention is a compound represented by the following structural formula:

and having geranylgeranylacetone is as its chemical name.

In the whitening embellisher according to the present invention, the amount of teprenone to be used can not be absolutely specified because it varies according to the form of preparation. However, it is generally 0.1–20 wt. %, preferably 0.5–10 wt. %, more preferably 1.0–10 wt. % based on the whole weight of the whitening embellisher.

The composition according to the present invention is characterized by the fact that teprenone is mixed with one or more substances selected from kojic acid, L-ascorbic acid, arbutin and chemical derivatives thereof. Among the latter substances, kojic acid or L-ascorbic acid is a particularly preferred compound.

In the composition according to the present invention, the amount of teprenone to be used can not be absolutely specified because it varies according to the form of preparation. However, it is generally 0.1–20 wt. %, preferably 0.5–10 wt. %, more preferably 1.0–10 wt. % based on the whole weight of the composition.

In the composition of the present invention, the amount of kojic acid, L-ascorbic acid, arbutin and/or a chemical derivative thereof to be used is generally 0.1–20 wt. %, preferably 0.5–10 wt. %, more preferably 1.0–10 wt. % based on the whole weight of the composition.

No particular limitation is imposed on the forms of the whitening embellisher and whitening and beautifying composition according to the present invention. They can be formulated in desired forms including cream, ointment, lotion, milky lotion, plasters, etc. No specific limitation is also imposed on the forms of preparations for a bath according to the present invention. They may be formulated into the conventionally-used forms. As base materials for these preparations, there may be used a wide variety of materials used conventionally in cosmetics, quasi-drugs, drugs and the like. The formulation of such whitening and beautifying preparations for external application or for a bath may follow the generally-performed production processes for cosmetics.

As exemplary base materials usable in the present invention, there may be mentioned known materials such as animal and vegetable oils, mineral oils, ester oils, waxes, higher alcohols, fatty acids, silicone oils, surfactants, phospholipids, alcohols, polyhydric alcohols, water-soluble polymers, clay minerals and purified water. Further, pH regulator, antioxidants, chelating agents, antiseptic and mildewproofing agents, coloring matter, perfume bases, and the like may be added suitably as needed. In addition, other active ingredients having a whitening and beautifying action or skin-beautifying action, blood circulation-facilitating agents, disinfectants, antiphlogistics, cell activators, vitamins, amino acids, moisturizers, keratolytics and the like may also be incorporated.

The external whitening embellisher according to the present invention may be used as cosmetics, and also as drugs.

The external preparation containing teprenone and having a whitening and beautifying action according to the present invention can be formulated in accordance with any process conventionally used. For example, in order to formulate a cream preparation, squalane, isopropyl myristate, cetostearyl alcohol, polyoxyethylene (20) sorbitan monostearate and the like are mixed with teprenone while heating them to about 80° C. to form an oil phase. On the other hand, glycerol and/or the like is dissolved in purified water, and the resulting solution is heated to about 80° C. to form an aqueous phase. The thus-formed aqueous phase is added to the oil phase under stirring. The resultant mixture is emulsified by a high-speed emulsifier and then cooled to room temperature, thereby permitting the provision of the cream preparation containing teprenone therein.

The whitening and beautifying preparation suitable for use in a bath according to the present invention means a preparation which can be dissolved in hot water in a bathtub upon bathing to use it, and can be provided as tablets, granules, powder, liquid or the like. It can be formulated according to any process generally used. It is however essential to add a surfactant because teprenone is insoluble in water.

The effect of the whitening and beautifying preparation suitable for external application or use in a bath is considered to be attributed to the fact that the preparation inhibits the biosynthesis of tyrosinase in pigment cells. As described in the following experimental examples, this is suggested from the fact that the external application of the compound according to the present invention reduces the amount of melanin without exhibiting any cytotoxicity.

More specifically, teprenone did not exhibit any action to inhibit the enzyme activity on an enzyme, tyrosinase, derived from mushroom even in a concentration of 0.01–0.1%. On the other hand, with respect to its effect to restrain the production of melanin on B16 melanoma cells derived from a mouse, it was recognized that the production of melanin is restrained by 85%, 80% and 70%, respectively, in sample concentrations of $1\times10^{-4}\%$, $2\times10^{-4}\%$ and $3\times10^{-4}\%$ to control. In this experiment, the amount of proteins in the B16 melanoma cells did not change, the amount of mitochondria tended to increase, and no cytotoxicity was recognized in these sample concentrations. The amount of tyrosinase in the B16 melanoma cells in each culture system added with teprenone was determined by SDS-PAGE (sodium dodecyl sulfate polyacrylamide gel electrophoresis). As a result, it was found that the amount of tyrosinase is decreased in proportion to the concentration of teprenone added. When the B16 melanoma cells in which the amount of melanin had been restrained by the addition of teprenone were cultured again in a system containing no teprenone, the amount of melanin in the cells was greatly increased. Therefore, it has also been confirmed that this inhibiting action is a reversible inhibiting action.

A detailed knowledge relating to the action mechanisms as to the inhibition of the synthesis of a tyrosinase enzyme group by teprenone used in the preparations according to the present invention and the restraint of melanin production owing to this inhibition is unapparent at present. Teprenone according to the present invention is however considered to act like a scavenger on active enzymes and radical products, which serve as inducers for tyrosinase in pigment cells.

The whitening and beautifying composition according to the present invention is considered to develop its effect owing to the synergism of teprenone with other substance having a whitening and beautifying action, such as kojic acid or L-ascorbic acid. The reason is considered to be that the action of kojic acid or L-ascorbic acid resides in inhibiting the activity of tyrosinase, and the action of teprenone resides in inhibiting the synthesis of tyrosinase. More specifically, since teprenone inhibits the synthesis of tyrosinase, the amount of tyrosinase in cells is decreased, and moreover the activity of the tyrosinase produced is inhibited by kojic acid or L-ascorbic acid. It is therefore inferred that both compounds would strongly inhibit the synthesis of melanin.

How far the combined use of teprenone with the whitening and beautifying material already known, which is an object of the whitening and beautifying composition according to the present invention, raises the limit of potency of the known material is demonstrated by an experiment. Namely, when B16 melanoma cells derived from a mouse were cultured for 5 days in a medium added with kojic acid in an amount of 0.01–0.03%, the amount of melanin was reduced to 98–80% compared with the control culture cells, while the amount of melanin in the melanoma cells in a culture system added further with $1\times10^{-4}$–$3\times10^{-4}\%$ (1–3 ppm) of teprenone was decreased to 65–63%. When arbutin is used for attaining the same effect of the combined use as kojic acid, it is essential to add arbutin in a concentration of $1\times10^{-3}$–$3\times10^{-3}\%$ (10–30 ppm).

It has thus been confirmed that the combined use of teprenone according to the present invention with the already known material is excellent in effectiveness. This is attributed to the fact that teprenone according to the present invention is an inhibitor against the synthesis of tyrosinase, which has a unique feature from the viewpoint of physical properties and also of action mechanism. As described above, the whitening embellisher, and whitening and beautifying composition according to the present invention have an action to strongly inhibit the production of melanin in the epithelia. Therefore, the color of spot portions caused by abnormal pigmentation can be lightened quickly, the pigmentation due to sunburn can be prevented highly, and the pigmentation caused by sunburn can be faded more quickly by using them after the sunburn.

The present invention will hereinafter be described more specifically by the following examples and utility tests. It should however be borne in mind that the present invention is not limited to these examples only.

EXAMPLE 1

Cream containing 1% of teprenone

TABLE 1

| Raw material | Proportion (wt. %) |
| --- | --- |
| 1) Teprenone | 1.0 |
| 2) Squalane | 10.0 |
| 3) Isopropyl myristate | 7.0 |
| 4) Behenyl alcohol | 1.0 |
| 5) Cetostearyl alcohol | 5.5 |
| 6) Glycerol monostearate | 2.0 |
| 7) d-α-Tocopherol | 0.05 |
| 8) POE (20) sorbitan monostearate | 2.0 |
| 9) Xanthan gum | 0.1 |
| 10) 1,3-Butylene glycol | 2.0 |
| 11) Glycerol | 3.0 |
| 12) Sorbitol | 5.0 |
| 13) Paraben | 0.2 |
| 14) Purified water | To 100.0 |

<Preparation process>

Raw materials 1–8 were weighed out and heated to 80°–90° C. into a solution, thereby providing an oil phase. Raw materials 9 and 10 were mixed with each other, and raw materials 11–14 were added thereto. The resulting mixture was heated to 80°–90° C. and stirred into a solution, thereby providing an aqueous phase. The oil phase was added to the aqueous phase under stirring to emulsify them by a homomixer. The resulting emulsion was then cooled to room temperature under stirring, thereby obtaining a cream containing 1% of teprenone.

EXAMPLE 2

Ointment containing 3% of teprenone

TABLE 2

| Raw material | Proportion (wt. %) |
| --- | --- |
| 1) Teprenone | 3.0 |
| 2) PLASTIBASE 50W | 97.0 |

<Preparation process>

Raw material 1 was weighed out, and raw material 2 was gradually added thereto under stirring or kneading. The resulting mixture was thoroughly kneaded to obtain an ointment containing 3% of teprenone as an intimate mixture.

EXAMPLE 3

Lotion containing 0.5% of teprenone

TABLE 3

| Raw material | Amount formulated |
| --- | --- |
| 1) Teprenone | 0.5 g |
| 2) Purified soybean lecithin | 0.7 g |
| 3) Ethanol | 10.0 ml |
| 4) d-α-Tocopherol | 0.02 g |
| 5) Propylene glycol | 3.0 g |
| 6) Xanthan gum | 0.1 g |
| 7) Paraben | 0.1 g |
| 8) Purified water | To 100.0 ml |

<Preparation process>

Raw materials 6 and 7 were mixed with raw material. 5, and 40 ml of purified water was added to the mixture. The resultant mixture was heated to 85° C. and stirred into a solution. The resulting solution was then cooled to room temperature. Raw materials 1–4 were mixed with each other, and the resulting mixture was heated to 60° C. into a solution. The thus-formed solution was added to 40 ml of purified water under stirring to prepare an emulsion. The aqueous solution previously prepared was mixed with the emulsion, and the resulting mixture was added with purified water to 100 ml, thereby obtaining a lotion containing 0.5% of teprenone.

EXAMPLE 4

Bath preparation

TABLE 4

| Raw material | Amount formulated |
| --- | --- |
| 1) Sodium sulfate | 69.2 g |
| 2) Sodium hydrogencarbonate | 24.0 g |
| 3) Sodium chloride | 4.0 g |
| 4) Teprenone | 1.0 g |
| 5) Polyoxyethylene hardened castor oil | 0.8 g |
| 6) Perfume base | 1.0 g |

<Preparation process>

The above-described compounds were intimately mixed with each other to obtain a a bath preparation containing teprenone.

Comparative Example 1

Comparative Example 1 was performed in the same manner as in Example 1 in accordance with the following formulation:

TABLE 5

| Raw material | Proportion (wt. %) |
| --- | --- |
| 1) Squalane | 10.0 |
| 2) Isopropyl myristate | 7.0 |
| 3) Behenyl alcohol | 1.0 |
| 4) Cetostearyl alcohol | 5.5 |
| 5) Glycerol monostearate | 2.0 |
| 6) d-α-Tocopherol | 0.05 |
| 7) POE (20) sorbitan monostearate | 2.0 |
| 8) Xanthan gum | 0.1 |
| 9) 1,3-Butylene glycol | 2.0 |
| 10) Glycerol | 3.0 |
| 11) Sorbitol | 5.0 |
| 12) Paraben | 0.2 |
| 13) Disodium hydrogenphosphate | Proper amount |
| 14) Purified water | To 100.0 |

Utility Test 1:

<Testing method>

The two preparations obtained in Example 1 and Comparative Example 1 were tested in the following manner. Namely, 19 women of 22–49 years of age were chosen as panelists. Proper amounts of the preparations were coated on the face and 4 portions of the forearms of each panelist after washing the face twice in the morning and evening every day each for 3 weeks and over 6 weeks in total to evaluate their effects as a whitening embellisher both in accordance with the following standard and by a color difference meter. Incidentally, this test was conducted by a blind test in which the panelists were left uninformed of the formulations of the samples.

<Standard>

+: Spots and freckles became inconspicuous;
±: Spots and freckles became scarcely conspicuous;
−: Not changed.

<Results of test>

With respect to each panelist, the lightness of the skin at the portions of the forearms before and after the use of each preparation were measured by a color difference meter, and the effect on the spots and freckles on the face was observed. The results shown in the following Table 6 were obtained.

TABLE 6

| Sample | Whitening and beautifying effect | | | Lightness of skin YI (Average value of (color difference)) | |
|---|---|---|---|---|---|
| | + | ± | − | Before coating | After coating |
| Example 1 | 11 | 7 | 1 | 58.3 | 47.7 |
| Comparative Example 1 | 0 | 2 | 17 | 62.5 | 60.5 |

As apparent from these results, the cosmetic preparation according to the present invention is excellent in whitening and beautifying effect and is effective in preventing and improving the blackening and darkening of the skin, spots, and freckles, which are caused by sunburn, aging and/or the like.

EXAMPLE 5

Teprenone cream containing 1% of L-ascorbic acid

TABLE 7

| <Formulation> | |
|---|---|
| Raw material | Proportion (wt. %) |
| 1) Teprenone | 1.0 |
| 2) L-Ascorbic acid | 1.0 |
| 3) Squalane | 10.0 |
| 4) Isopropyl myristate | 7.0 |
| 5) Behenyl alcohol | 1.0 |
| 6) Cetostearyl alcohol | 5.5 |
| 7) Glycerol monostearate | 2.0 |
| 8) d-α-Tocopherol | 0.05 |
| 9) POE (20) sorbitan monostearate | 2.0 |
| 10) Xanthan gum | 0.1 |
| 11) 1,3-Butylene glycol | 2.0 |
| 12) Glycerol | 3.0 |
| 13) Sorbitol | 5.0 |
| 14) Paraben | 0.2 |
| 15) Disodium hydrogenphosphate | Proper amount |
| 16) Purified water | To 100.0 |

<Preparation process>

Raw materials 1 and 3–9 were weighed out and heated to 80°–90° C. into a solution, thereby providing an oil phase. Raw materials 10 and 11 were mixed with each other, and raw materials 12–14 and 16 were added thereto. The resulting mixture was heated to 80°–90° C. and stirred into a solution,, thereby providing an aqueous phase. The thus-obtained aqueous phase was added with raw materials 2 and 15. The oil phase was added to the aqueous phase under stirring to emulsify them by a homomixer. The resulting emulsion was then cooled to room temperature under stirring, thereby obtaining a cream containing 1% of teprenone and 1% of L-ascorbic acid.

EXAMPLE 6

Teprenone cream containing 1% of Kojic acid

TABLE 8

| <Formulation> | |
|---|---|
| Raw material | Proportion (wt. %) |
| 1) Teprenone | 1.0 |
| 2) Kojic acid | 1.0 |
| 3) Squalane | 10.0 |
| 4) Isopropyl myristate | 7.0 |
| 5) Behenyl alcohol | 1.0 |
| 6) Cetostearyl alcohol | 5.5 |
| 7) Glycerol monostearate | 2.0 |
| 8) d-α-Tocopherol | 0.05 |
| 9) POE (20) sorbitan monostearate | 2.0 |
| 10) Xanthan gum | 0.1 |
| 11) 1,3-Butylene glycol | 2.0 |
| 12) Glycerol | 3.0 |
| 13) Sorbitol | 5.0 |
| 14) Paraben | 0.2 |
| 15) Purified water | To 100.0 |

<Preparation process>

Raw materials 1 and 3–9 were weighed out and heated to 80°–90° C. into a solution, thereby providing an oil phase. Raw materials 10 and 11 were mixed with each other, and raw materials 12–15 were added thereto. The resulting mixture was heated to 80°–90° C. and stirred into a solution, thereby providing an aqueous phase. The thus-obtained aqueous phase was added with raw material 2. The oil phase was added to the aqueous phase under stirring to emulsify them by a homomixer. The resulting emulsion was then cooled to room temperature under stirring, thereby obtaining a cream containing 1% of teprenone and 1% of kojic acid.

EXAMPLE 7

Teprenone a bath preparation containing 1.0% of L-ascorbic acid

TABLE 9

| <Formulation> | |
|---|---|
| Raw material | Proportion (wt. %) |
| 1) Sodium sulfate | 69.2 |
| 2) Sodium hydrogencarbonate | 24.0 |
| 3) Sodium chloride | 3.0 |
| 4) Teprenone | 1.0 |
| 5) L-Ascorbic acid | 1.0 |
| 6) Polyoxyethylene hardened castor oil | 0.8 |
| 7) Perfume base | 1.0 |

<Preparation process>

The above-described composition was intimately mixed to obtain an L-ascorbic acid-containing teprenone preparation suitable for use in a bath.

EXAMPLE 8

Teprenone cream containing 1% of d-δ-tocopherol

TABLE 10

| <Formulation> | |
|---|---|
| Raw material | Proportion (wt. %) |
| 1) Teprenone | 1.0 |
| 2) d-δ-Tocopherol | 1.0 |

TABLE 10-continued

| Raw material | Proportion (wt. %) |
|---|---|
| 3) Squalane | 10.0 |
| 4) Isopropyl myristate | 7.0 |
| 5) Behenyl alcohol | 1.0 |
| 6) Cetostearyl alcohol | 5.5 |
| 7) Glycerol monostearate | 2.0 |
| 8) POE (20) sorbitan monostearate | 2.0 |
| 9) Xanthan gum | 0.1 |
| 10) 1,3-Butylene glycol | 2.0 |
| 11) Glycerol | 3.0 |
| 12) Sorbitol | 5.0 |
| 13) Paraben | 0.2 |
| 14) Purified water | To 100.0 |

<Preparation process>

Raw materials 1–8 were weighed out and heated to 80°–90° C. into a solution, thereby providing an oil phase. Raw materials 9 and 10 were mixed with each other, and raw materials 11–14 were added thereto. The resulting mixture was heated to 80°–90° C. and stirred into a solution, thereby providing an aqueous phase. The oil phase was added to the aqueous phase under stirring to emulsify them by a homomixer. The resulting emulsion was then cooled to room temperature under stirring, thereby obtaining a cream containing 1% of teprenone and 1% of d-δ-tocopherol.

Comparative Example 2–5

Comparative Examples 2–5 were performed in the same manner as in Examples 5–6 in accordance with their corresponding formulations shown in the following Table 11:

TABLE 11

| Raw material | Comp. Ex. 2 | Comp. Ex. 3 | Comp. Ex. 4 | Comp. Ex. 5 |
|---|---|---|---|---|
| L-Ascorbic acid | — | 1.0 | — | — |
| Kojic acid | — | — | 1.0 | — |
| Teprenone | — | — | — | 1.0 |
| Squalane | 10.0 | 10.0 | 10.0 | 10.0 |
| Isopropyl myristate | 7.0 | 7.0 | 7.0 | 7.0 |
| Behenyl alcohol | 1.0 | 1.0 | 1.0 | 1.0 |
| Cetostearyl alcohol | 5.5 | 5.5 | 5.5 | 5.5 |
| Glycerol monostearate | 2.0 | 2.0 | 2.0 | 2.0 |
| d-α-Tocopherol | 0.05 | 0.05 | 0.05 | 0.05 |
| Sorbitan fatty acid ester | 2.0 | 2.0 | 2.0 | 2.0 |
| Xanthan gum | 0.1 | 0.1 | 0.1 | 0.1 |
| 1,3-Butylene glycol | 2.0 | 2.0 | 2.0 | 2.0 |
| Glycerol | 3.0 | 3.0 | 3.0 | 3.0 |
| Sorbitol | 5.0 | 5.0 | 5.0 | 5.0 |
| Paraben | 0.2 | 0.2 | 0.2 | 0.2 |
| Disodium hydrogenphosphate | — | Proper amount | — | — |
| Purified water | To 100 | To 100 | To 100 | To 100 |

Utility Test 2:
<Testing method>

The six preparations obtained in Examples 5–6 and Comparative Examples 2–5 were tested in the following manner. Namely, 19 women of 22–49 years of age were chosen as panelists. Proper amounts of the preparations were coated on the face and 6 portions of the forearms of each panelist after washing the face twice in the morning and afternoon every day each for 3 weeks and over 18 weeks in total to evaluate their effects as a whitening embellisher both in accordance with the following standard and by a color difference meter.

<Standard>
+: Spots and freckles became inconspicuous;
±: Spots and freckles became scarcely conspicuous;
−: Not changed.

<Results of test>

The six creams prepared in accordance with the formulations of Examples 5–6 and Comparative Examples 2–5 were separately applied to the 19 panelists by a blind test in which the panelists were left uninformed of the formulations of the samples. With respect to each panelist, each preparation was used twice a day for 3 weeks, and the lightness of the skin at the portions of the forearms before and after the use of the preparation were measured by a color difference meter. Further, the effect on the spots and freckles on the face was observed. The results shown in the following Table 12 were obtained.

TABLE 12

| Sample | Whitening and beautifying effect | | | Lightness of skin YI (Average value of color difference) | | |
|---|---|---|---|---|---|---|
| | + | ± | − | Before coating | After coating | Improvement degree (%) |
| Example 5 | 13 | 6 | 0 | 59.8 | 47.1 | 21.2 |
| Example 6 | 16 | 2 | 1 | 59.2 | 43.0 | 27.4 |
| Comparative Example 2 | 0 | 2 | 17 | 62.5 | 60.5 | 3.2 |
| Comparative Example 3 | 5 | 6 | 8 | 61.3 | 55.4 | 9.6 |
| Comparative Example 4 | 8 | 5 | 6 | 60.9 | 49.8 | 18.2 |
| Comparative Example 5 | 11 | 7 | 1 | 58.3 | 47.7 | 18.2 |

$$\text{Improvement degree} = 100 - \frac{\text{YI after coating}}{\text{YI before coating}} \times 100$$

As apparent from Table 12, the cosmetic preparations according to the present invention, which have been obtained in Example 5–6, are far more excellent in whitening and beautifying effect and are effective in preventing and improving the blackening and darkening of the skin, spots, and freckles, which are caused by sunburn, aging and/or the like.

What is claimed is:

1. A method for inhibiting production of melanin in epithelia of an individual, which comprises applying teprenone to skin of the individual.

2. The method as claimed in claim 1, which the teprenone is a preparation selected from the group consisting of tablets, granules, powder and liquid.

3. The method as claimed in claim 1, which the teprenone is a preparation selected from the group consisting of cream, ointment, lotion and plaster.

4. The method as claimed in claim 3, wherein the lotion is a milky lotion.

* * * * *